US005976780A

United States Patent [19]
Shah

[11] Patent Number: 5,976,780
[45] Date of Patent: Nov. 2, 1999

[54] ENCAPSULATED CELL DEVICE

[76] Inventor: Kumarpal A. Shah, 28 Ridge Rd., Searingtown, N.Y. 11507

[21] Appl. No.: 09/089,174

[22] Filed: Jun. 2, 1998

Related U.S. Application Data

[63] Continuation-in-part of application No. 08/680,795, Jul. 16, 1996, Pat. No. 5,837,444.

[51] Int. Cl.$^6$ .............................. A01N 1/02; C12N 11/04
[52] U.S. Cl. .......................... 435/1.1; 424/93.7; 424/424; 424/425; 427/2.14; 427/2.24; 435/177; 435/178; 435/182; 435/400
[58] Field of Search ................................... 424/93.7, 424, 424/425; 427/2.14, 2.24; 435/1.1, 177, 178, 182, 400

[56] References Cited

U.S. PATENT DOCUMENTS

| | | |
|---|---|---|
| 4,352,883 | 10/1982 | Lim . |
| 4,391,909 | 7/1983 | Lim . |
| 5,002,661 | 3/1991 | Chick et al. . |
| 5,144,016 | 9/1992 | Skjak-Braek et al. . |
| 5,459,054 | 10/1995 | Skjak-Braek et al. . |
| 5,573,934 | 11/1996 | Hubbell et al. ........................ 435/177 |
| 5,578,314 | 11/1996 | Cochrum et al. . |
| 5,620,883 | 4/1997 | Shao et al. . |
| 5,653,687 | 8/1997 | Mills et al. . |
| 5,653,688 | 8/1997 | Mills et al. . |
| 5,693,514 | 12/1997 | Dorian et al. . |
| 5,713,888 | 2/1998 | Neuenfeldt et al. . |
| 5,837,444 | 11/1997 | Shah ........................................ 435/4 |

OTHER PUBLICATIONS

Chapekar, M.S. Regulatory concerns in the development of Biomedical Materials Research(Applied Biomaterials) vol. 33, 199–203, 1996.

Soon–Shiong P., Feldman E., Nelson R., Heintz R., Yao L., Zheng T., Merideth N., Skaj–Braek G., Espevik T. et al 1993 "Long–term reversal of diabetes by the injection of immunoprotected islets" Proceedings of NA of Sci., USA 90(12): "Abstract".

Soon–Shiong P., et al "Insulin independence in a type 1 diabetic patient after encapsulated islet cell transplantation." Lancet, 343: 950–51, 1994.

NBC Nightly News Transcript: Revolutionary new transplant technologies offering new hope to severe diabetics Nov. 20, 1995, pp. 6–7.

Internet News, "The Islet Foundation . . . A Final Push in the Cure for Diabetes", p. 1.

Sun Y., Xiaojun M., Zhou D., Vacek I., Sun A.M. "Normalization of diabetes in spontaneously diabetic cyanomolgus monkeys by xenografts of microencapsulated porcine islets without immunosuppression", J. Clin. Invest. 98, 1417–1422.

Lanza R.P., Soloman B.A., Chnick W.L. "Hollow fibers and macroencapsulation"—Methods in cell transplantation edited by C. Ricordi, 1995, R.G. Landes. pp. 611–615.

Ricordi C., Lacy P.E., Fink E.H., Clark B.J., and Sharp D. "Automated method for isolation of human pancreatic islets" Diabetes, vol. 37: 413–20, 1988.

Bretzel R.G., Alejandro R., Hering B.J., Van Suylichem P.T.R. & Ricordi C., "Clinical Islet Transplantation: Guidelines for Islet Quality Control", Transplantation Proceedings, vol. 26, No. 2 (Apr.), 1994: 388–392.

Calafiore R., Basta G. "Microencapsulation of pancreatic islets: Theoretical principles, technologies and practice," Methods in Cell Transplantation, edited by C. Ricordi, 1995, R.G. Landes Co., 587–609.

Arita S., Thompson K., Stein E., Matsuda N., Cochrum K., Jemtrud S., Une S., Kawahara T., Shevlin L., Trieu C., Mullen Y., "In vitro activation of human lymphocytes by crude and purified alginates" Transplantation proceedings, 29, 2125, 1997.

Zimmermann, U., Klock, G., Federlin, K., et al, "Production of mit ogen–contamination free alginates with variable ratios of mannuronic acid to guluronic acid by Free Flow Electrophoresis," Electrophoresis, [summary], vol. 13, p. 269, 1992.

Weber C.J. et al, "CTLA4–Ig Prolongs Survival of Microencapsulated Neonatal Porcine Islet Xenografts in Diabetic NOD Mice", Cell Transplantation, 1997, pp. 505–508, vol. 6, No. 5.

Harlan D.M. et al, "Tolerance and Costimulatory Pathway", Pancreatic Islet Transplantation: vol. II, Immunomodulation of Pancreatic Islets, edited by Lanza R.P. et al, 1994, R. G. Landes Co., pp. 141–151.

Mooney D. et al, "Engineering Biomaterials for Tissue Engineering: The 10–100 Micron Size Scale", The Biomaterial Engineering Handbook, edited by Bronzino J., CRC Press, Inc., 1995, pp. 1609–1618.

Smidsrod O. et al, "Alginate as Immobilization Matrix for Cells", Trends in Biotechnology, 1990, vol. 8, No. 3 (74), pp. 71–78.

"Pancreatic Islet Transplantation: vol. III, Immunoisolation of Pancreatic Islets", edited by Lanza R.P. et al, 1994, R.G. Landes, pp. 1–179.

(List continued on next page.)

Primary Examiner—David Saunders
Attorney, Agent, or Firm—Shenier & O'Connor

[57] ABSTRACT

A macroencapsulation device for somatic cells using ultrapurified Na alginate and polysulfone hollow fibers of 30 kDa molecular weight cutoff. Ultrapurified Na alginate material is used which has a high 'G' content, low endotoxin content, low divalent metal toxins and low protein impurities. Islet cells prior to being encapsulated, are irrigated with Hank's modified solution (without Ca and Mg) containing gentamycin, vancomycin and amphotericin B and then passed through a leukoabsorb filter to reduce the donor antigen load of passenger leukocytes and to reduce the bioburden of microorganisms including viruses. Encapsulation is done in RPMI 1640 tissue culture fluid containing necessary nutritional supplements and ATP source of energy. The open ends of the fiber are covered with a porous membrane. To further improve biocompatibility, the outer wall of the polysulfone is lightly gelled with alginate gel. Such double gelled, encapsulated fibers do not affect diffusion of glucose or insulin across the hollow fibers.

38 Claims, 4 Drawing Sheets

OTHER PUBLICATIONS

Benson J.P. et al, "Towards the Development of a Bioartificial Pancreas: Effects of Poly–L–Lysine on Alginate Beads with BTC3 Cells", Cell Transplantation, 1997, Abstract, vol. 6, No. 4.

Kaneto H. et al, "Apoptotic Cell Death Triggered by Nitric Oxide in Pancreatic B Cells", Diabetes 1995, vol. 44, pp. 733–738.

Kulseng B., Thu B., Espevik T., and Skjak–Braek G. "Alginate polylysine microcapsules as immune barrier: Permeability of cytokines and immunoglobulins over the capsule membrane" Cell transplantation, vol. 6, No. 4, pp. 387–394, 1997.

Dallman M.J. "Cytokines in Transplantation" in Pancreatic Islet Transplantation: vol. II, Immunomodulation of pancreatic islets, edited by Lanza R.P. and Chick W.L., 1994, R.G. Landes Co., pp. 41–49.

Vanholder R., Van Loo A. and Ringoir S. "Clinical experience with polysulfone: 10 yrs"Clinical Nephrology, vol. 42, Suppl. No. 1–1994 (S13–S20).

Cheung S.C., Tai J., Tze W.J., "Effect of molecular weight exclusion of polysulfone fibers on macroencapsulated pig islet xenograft function in diabetic mice", Transplantation Proceedings, 29, 2144–2145, 1997.

Tze W.J., Cheung J.T., Bissada N., Tsang A., Yep W. "Prolongation of pig islet xenograft survival in polysulfone fiber coil", Transplantation Proceedings, vol. 26:6, 1994, 3510–3511.

Platt J.L. "Islet xenotransplantation: How sweet it is" J. Cli. Invest., vol. 98, No. 6, 1996, 1273–74.

Ricordi C. "Human islet cell transplantation: new perspectives for an old challenge", Diabetes Reviews, vol. 4, No. 3, 1996, pp. 356–369.

Rubin H.J., Altman W.M., and Mendelson D.N. "Health care expenditures for people with diabetes mellitus", J. Clin. Endocrinol Metab 78: 809A–809F, 1994.

Porte, Jr., D., Schwartz M.W., "Diabetes complications: Why is glucose potentially toxic?" Science, vol. 272, May 3, 1996, pp. 699–700.

Peer to Peer, "Clinical Highlights of the American Diabetes Association 53rd Annual Meeting", Las Vegas, Nevada, Jun. 12–15, 1993, p. 1–16, vol. 5, No. 4, Autumn, 1993.

Thomas T.F., Henretta L.J., Pitiman K. and Thomas J. Reversal of type 2 (NIDDM) diabetes by pancreatic islet transplantation: An emerging concept of an enigmatic disease, Transplantation Proceedings, vol. 27, No. 6, 1995, pp. 3167–3169.

Ricordi, C. et al, "Human Islet Allografts in Patients With Type 2 Diabetes Undergoing Liver Transplantation", Transplantation Proceedings, vol. 63, No. 3, pp. 473–475, 1997.

Aubuchon J.P., Dodd R.Y., "Inactivation of microbial contaminants of blood components"—Clinics in laboratory medicine, vol. 12, No. 4, 1992, pp. 787–803.

Meryman H.T. "Transfusion–induced alloimmunization and immunosuppression and the effect of leukocyte depletion", pp. 180–193.

Colton, Clark K., "Implantable Biohybrid Artificial Organs", Cell Transplantation, vol. 4, No. 4, pp. 415–436, 1995.

Gill, Ronald G. & Wolf, Leslie, "Immunobiology of Cellular Transplantation", Cell Transplantation, vol. 4, pp. 361–370, 1995.

Douglas A. Holt et al, "Infectious Issues in Human Fetal Neural Transplantation", Cell Transplantation, vol. 6, No. 6, pp. 553–556, 1997.

Tyden, Gunnar, M.D., et al, "Recurrence of Autoimmune Diabetes Mellitus in Recipients of Cadaveric Pancreatic Grafts", The New England Journal of Medicine, pp. 860–863, Sep. 1996.

Eisenbarth, George S., M.D., Stegall, Mark, M.D., "Islet and Pancreatic Transplantation—Autoimmunity and Alloimmunity", New England Journal of Medicine, pp. 888–890, Sep. 19, 1996.

Crawford M. et al, "Autoimmune Islet Damage Mediated by Insulin–Specific T Cells", Transplantation Proceedings, 1997, vol. 29, pp. 758–759.

Cole D.R. et al, "Transplantation of Microencapsulated Pancreatic Islets in BB/E Diabetic Rats: Mechanisms of Graft Failure", Diabetalogica, 1989, Vo. 32, p. 477A, Abstract 101.

Lanza R.P. et al, "Xenogeneic Humoral Responses to Islets Transplanted in Biohybrid Diffusion Chambers", Transplantation, 1994, vol. 57, No. 9, pp. 1371–1375.

Zekorn T. et al, "Protection of Islets of Langerhans from Interleukin–1 Toxicity by Artificial Membranes", Transplantation, 1990, vol. 50, No. 3, pp. 391–394.

Suzuki K. et al, "Number and Volume of Islets Transplanted in Immunobarrier Devices", Cell Transplantation, 1998, vol. 7, No. 1, pp. 47–52.

Committee Report, "Report of the Expert Committee on the Diagnosis and Classification of Diabetes Mellitus", Diabetes Care, 1997, vol. 20, No. 7, pp. 1183–1197.

De Vos, P. et al, "Obstacles in the Application of Microencapsulation in Islet Transplantatioin", The International Journal of Artificial Organs, vol. 16, No. 4, 1993, pp. 205–212.

Siebers U. et al, "Transplantation of Free and Microencapsulated Islets in Rats: Evidence for the Requirement of an Increased Islet Mass for Transplantation into the Peritoneal Site", The Intl. J. of Artificial Organs, vol. 16, No. 2, 1993, pp. 96–99.

Abstracts 4.1, 4.2, & 4.3, "Abstracts of the XVIth ESAO Congress—Brussels, Sep. 13–15, 1989", Artificial Pancreas, p. 566.

ENCAPSULATED CELL DEVICE

CROSS REFERENCE TO RELATED APPLICATIONS

This application is a continuation-in-part of my application Ser. No. 08/680,795 filed on Jul. 16, 1996 entitled Islet Cell Transplantation Machine for Diabetes Cure now U.S. Pat. No. 5,837,444.

BACKGROUND OF THE INVENTION

1. Field of the Invention

This invention relates to a macroencapsulated device for live cells. More particularly, it relates to materials and devices for transplantation and implantation of foreign cells and biological materials.

2. The Prior Art

Rapid advances in the field of biotechnology have lead to the development of novel biomaterials in which different types of somatic cells are encapsulated or combined with a variety of biopolymers in an attempt to restore, maintain, or improve tissue or organ function. The cell or biological component of the somatic cell-biomaterial combination secretes special chemicals or hormones while the biomaterial component protects the cells from immune attacks and at the same time is biocompatible with the host tissue. Tissue engineering approaches have microfabricated immunoprotective barriers around different types of somatic cells, namely neural, endocrine and hepatic cells. Immunoprotective barriers around donor islet cells as a therapeutic approach for the cure of diabetes is described as an example.

Islet cells have been encapsulated within alginate gel, with a technique called microencapsulation. U.S. Pat. No. 5,144,016 to Skjak-Braek et al discloses the chemistry, behavior and gelling properties of alginate material in different solutions. U.S. Pat. No. 4,352,883 to Lim discloses a method for encapsulating biological material such as living tissue, individual cells, hormones, enzymes or antibodies using Na alginate material. Microencapsulation of islet cells using alginate is disclosed in U.S. Pat. No. 4,391,909 to Lim. U.S. Pat. No. 5,459,054 to Skjak-Braek et al discloses encapsulation technology using purified Na alginate material with a high 'G' polymer content. The 'G' and 'M' polymer content of alginate is discussed in U.S. Pat. No. 5,578,314 to Cochrum et al, U.S. Pat. No. 5,693,514 to Dorian et al, and Sun Y. et al, Normalization of Diabetes in Spontaneously Diabetic Cynomologus Monkeys by Xenografts of Microencapsulated Porcine Islets without Immunosuppression (J. Clin. Invest., Volume 98, No. 6, 1996, 1417–1422).

The technique of gel suspending large numbers of islet cells together, for example within hollow fibers, is referred to as macroencapsulation. The use of synthetic material such as PAN-PVC hollow fibers for the construction of an artificial pancreas is disclosed in U.S. Pat. No. 5,002,661 to Chick et al. Islet cells encapsulated within PAN-PVC fibers is also discussed in R. P. Lanza et al, Hollow Fibers and Macroencapsulation (Methods in Cell Transplantation, pgs. 611–615, Chapter G16, R. G. Landes, 1995). However, the use of commercial grade or low purity alginate in these devices causes fibroblast overgrowth which leads to loss of porosity and death of the encapsulated cells. One group described using agarose to suspend pig islets within long strands of polysulfone fibers having pores with 100, 30, and 10 kDa cutoffs in S. C. Cheung et al, Effect of Molecular weight Exclusion of Polysulfone Fibers on Macroencapsulated Pig Islet Xenograft Function in Diabetic Mice (16 Transplantation Proceedings, pgs. 2144–2145, Elsevier Science Inc., N.Y., 1997). The long strands were bent into circular coils and their ends were sealed with heated clamps which resulted in fibrous build-up after only about 40 days of implantation. Other approaches for end sealing are disclosed in U.S. Pat. No. 5,653,687 and U.S. Pat. No. 5,653,888, both to Mills et al.

SUMMARY OF THE INVENTION

It is an object of the present invention to provide an encapsulated cell device which is biocompatible, safe and efficient.

It is another object of the present invention to provide encapsulated cells which are cost effective and clinically safe to use.

It is a further object to cap the open ends of such device with a porous membrane that enhances the functioning of the encapsulated cells.

It is yet another object of the present invention to reduce the donor antigen load and bioburden of pathogenic organisms including adventitious viruses.

It is still another object of the present invention to prevent donor antigens from leaking out and to prevent cytokines from diffusing in.

It is a further object of the present invention to inhibit complement activation at the implant site.

In applications requiring islet cells, for example, I achieve these objects by immunopurifying the isolated islet cells by first combining them with a mixture of Hank's solution enriched with fetal calf serum, adenine and antibiotics. The mixture is then passed through a leukoabsorb filter. The treated islet cells are combined with ultra purified Na alginate and aspirated into a hollow polysulfone fiber which is then dipped into a solution of CaCl to gel the alginate. The open ends of the fiber are covered with a membrane that cross-links to the alginate. The exterior of the fiber and the membrane are coated with Na alginate which is subsequently gelled.

This combination of materials provides excellent biocompatibility and superior control over pore size, the absence of which leads to immunorejection and cell death. The polysulfone material has a significant advantage over acrylic in that it does not interact with ACE inhibitor drugs, which can cause fatal allergic reactions. Biocompatability may be further enhanced by introducing a sulfonic group into the fiber to inhibit complement activation or adding a soluble sulfonic polymer to the Na alginate to further augment the inhibition.

Certain prior art attempts used fibers with 50–100 kDa pores which consistently allowed donor antigen leakage leading to host sensitization to MHC class antigens. In addition, this pore size permits cytokine diffusion which internally causes apoptic islet cell death and externally stimulates pericapsular fibrosis which clogs the pores necessary to supply the cells' nutritritional and metabolic requirements.

BRIEF DESCRIPTION OF THE DRAWINGS

In the accompanying drawings to which reference is made in the instant specification which is to be read in conjunction therewith and in which like reference numerals are used to indicate the parts in the various views.

DESCRIPTION OF THE PREFERRED EMBODIMENT

Figure 1A:
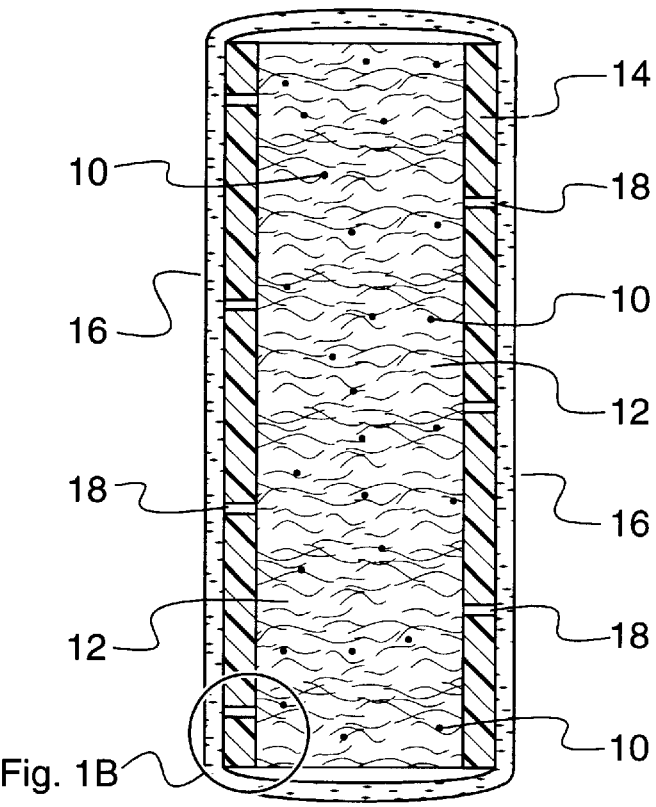
FIG. 1A is a cross-sectional view showing a macroencapsulation device according to the invention containing somatic cells.
Figure 1B:
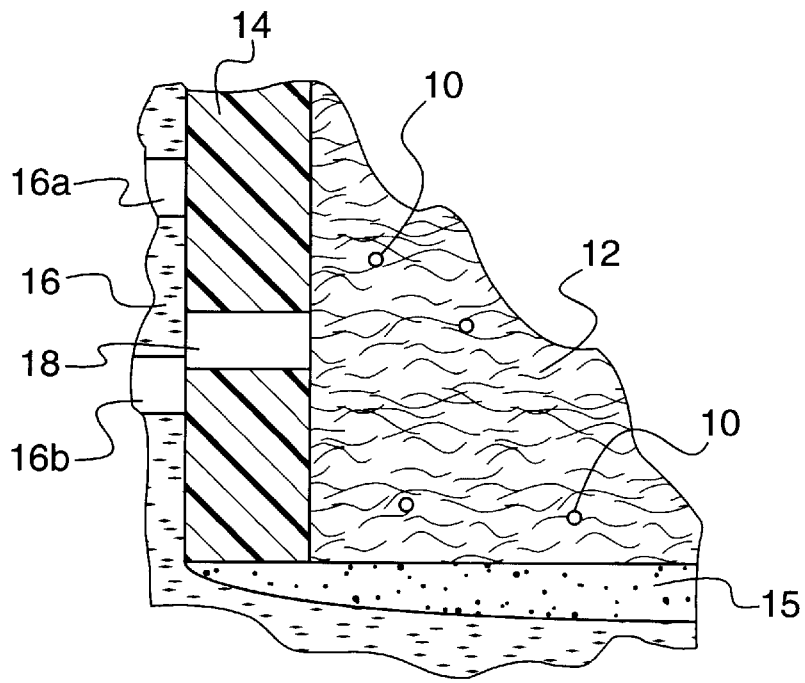
FIG. 1B is an enlarged cross-sectional view of a portion of the open end of the fiber.

As can be seen in FIGS. 1A and 1B, both natural and synthetic material are combined to encapsulate the cells, according to the invention. First, islet cells 10 are suspended in Na alginate gel 12 inside a polysulfone fiber 14 to improve islet viability. Second, the ends of fiber 14 are treated with a poly-L-lysine solution which forms a porous membrane 15 across the open end of the fiber. Third, the entire exterior of the fiber is coated with alginate 16 and gelled. The second and third steps improve biocompatibility and overall pore characteristics.

The Na alginate material is designated by the S.No. Property Product Code: Ultrapurified 28023316 and has the properties listed in Table 1.

TABLE 1

COMPOSITION OF ULTRAPURIFIED SODIUM ALGINATE (UP MVG)

| | | |
|---|---|---|
| 1. | G, GG, GGG CONTENTS | HIGH, >60% |
| 2. | VISCOSITY | 322mPas |
| 3. | pH | 5.9 |
| 4. | LOSS ON DRYING | 8.7% |
| 5. | PROTEIN CONTENT | <0.2% |
| 6. | ENDOTOXINS | 700 EU/g |
| 7. | HEAVY METALS (Cd,Cr,Cu, Mn, Pb, Ni, Zn, Hg) | <74 ppm |
| 8. | As | 0.5 ppm |
| 9. | Pb | 7 ppm |
| 10. | Fe | 58 ppm |

All of these factors may contribute to gel stability, strength and pore uniformity. Alginate used in the prior art is designated as low viscosity (20–200 mpas) and has a relatively high endotoxin content (<10,000 EU/g) and heavy metals content (<200 ppm) which can be toxic to cells. Surprisingly, applicant discovered that the characteristics of the UP MVG Alginate, particularly when combined with polysulfone and poly-L-lysine, provide unexpected results in macroencapsulation applications.

Optionally, a sulfonic compound is combined with the fiber and/or alginate to contribute to the inhibition of complement activation. A fiber containing a sulfonic group provides avid binding and inhibition of complement proteins. Both direct and alternate pathways of complement activation are inhibited. Furthermore, polymers bearing sulfonic acid groups have been found to decrease cytolytic complement activity. A soluble sulfonic polymer, for example sodium polystrene sulfonate, may be added to the alginate mixture. It is believed that polystrene sulfonate affects the C3 complement.

Figure 2:
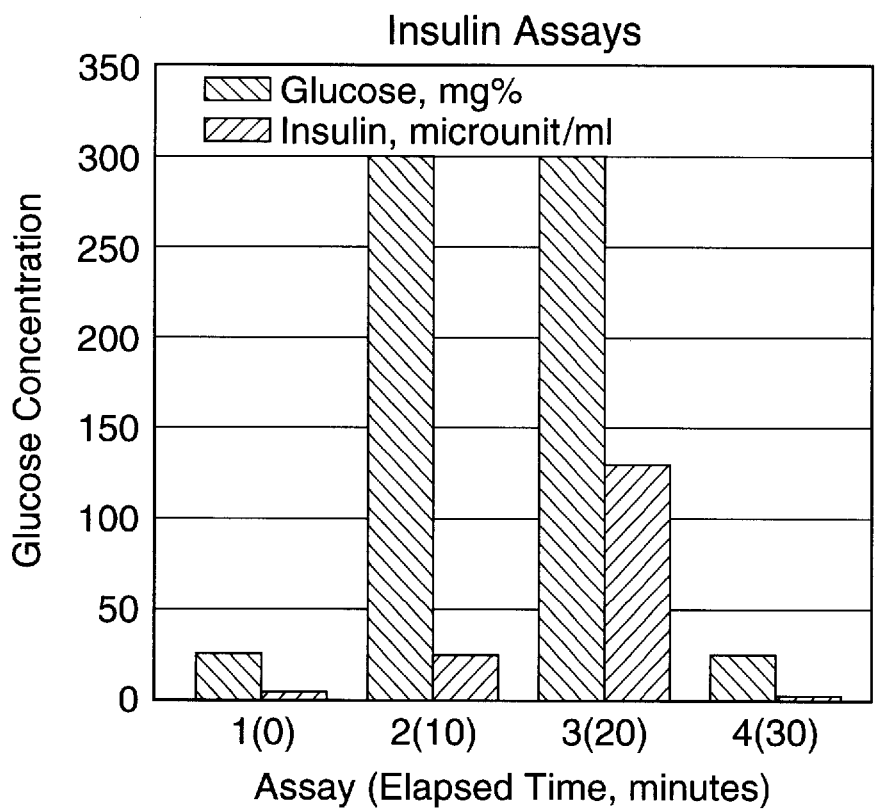
FIG. 2 is a graph illustrating the insulin kinetics of the encapsulated islet cells.

An encapsulated human islet cell device was studied in-vitro to assess its feed back relationship with glucose. Encapsulated human islet cells were exposed successively to glucose solutions of low concentration (sample 1,0 min.), high concentration (sample 2, 10 min.; sample 3, 20 min.) and then low glucose concentration (sample 4, 30 min.) Samples for determining insulin levels were obtained from the surrounding fluid. Insulin was assayed using Diagnosic Product Corp. (DPC) coated tube methodology and the results graphed in FIG. 2. The pore size distribution achieved with my combination of polysulfone, UP MVG and poly-L-lysine does not impede islet cell function or adversely affect the feedback kinetics with glucose.

EXAMPLE 1

Processing of Islet Cells Prior to Gel Encapsulation

Figure 4B:
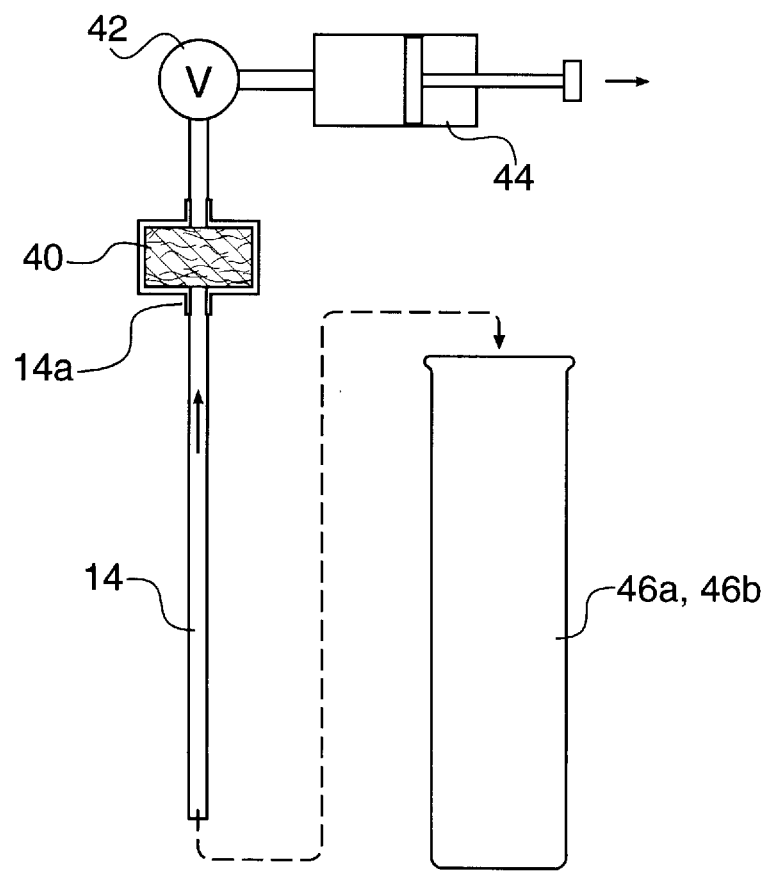
FIG. 4B shows the apparatus for aspirating the pretreated cells into the hollow fiber.
Figure 4A:
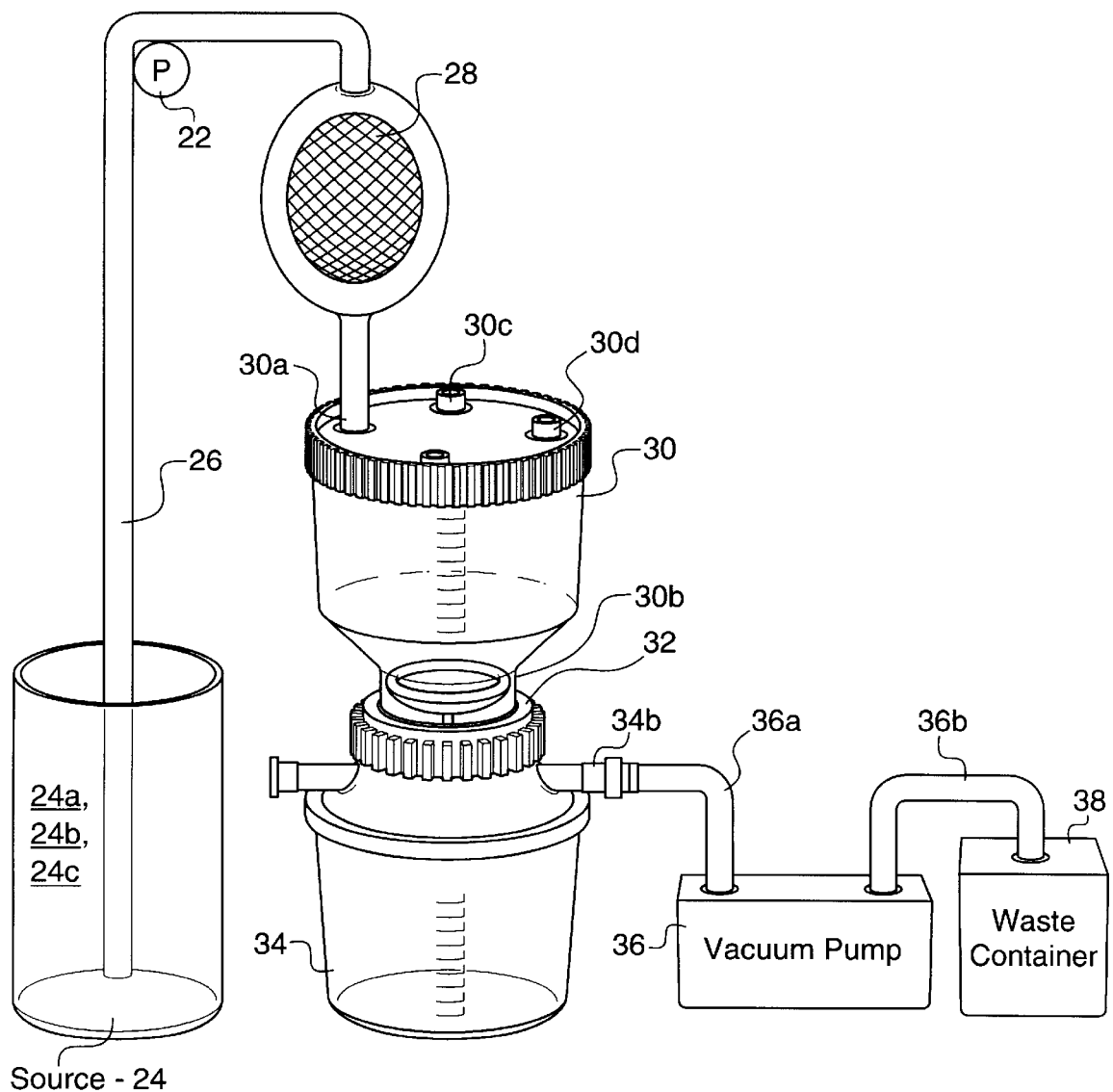
FIG. 4A shows an apparatus for pretreating the islet cells.

FIG. 4A shows an apparatus which is used to process the islet cells prior to encapsulation. A peristaltic pump 22 propels fluid from a source, generally referred to by reference numeral 24, through tubing 26 to leukoabsorb filter 28. Leukoabsorb filter 28 is connected to a polysulfone chamber 30 through a first port 30a. The bottom 30b of chamber 30 houses a 5 micron filter 32, beneath which is a flask 34 with an output vacuum port 34b. Vacuum port 34b is connected to inlet 36a of a vacuum pump 36. An outlet port 36b of vacuum pump 36 is connected to a waste container 38.

Initially, peristaltic pump 22 aspirates approximately 50 ml of 0.9% normal saline solution from a first source 24a at 10 ml per minute. Saline is passed through leukoabsorb filter 28 and polysulfone chamber 30 to wet filter 32. The entire solution is vacuum aspirated into waste container 38. Then, 50 ml or more of purified islet cell suspension in Hank's modified solution (without Ca and Mg), is aspirated by peristaltic pump 22 from a second source 24b at a rate of 2–3 ml per minute. The Hank's solution is enriched with 5% fetal calf serum and adenine as a source of energy. Gentamycin (50 mg/L), vancomycin (50 mg/L) or amphotericin B (2.5 mg/L) is added, although a combination of all three is particularly effective. The islet solution is passed slowly through leukoabsorb filter 28 into polysulfone chamber 30. Next, an additional 50 ml of Hank's modified solution is aspirated from a third source 24c into chamber 30. Vacuum aspiration is stopped when about 10 ml of solution remains in polysulfone chamber 30.

Figure 3A:
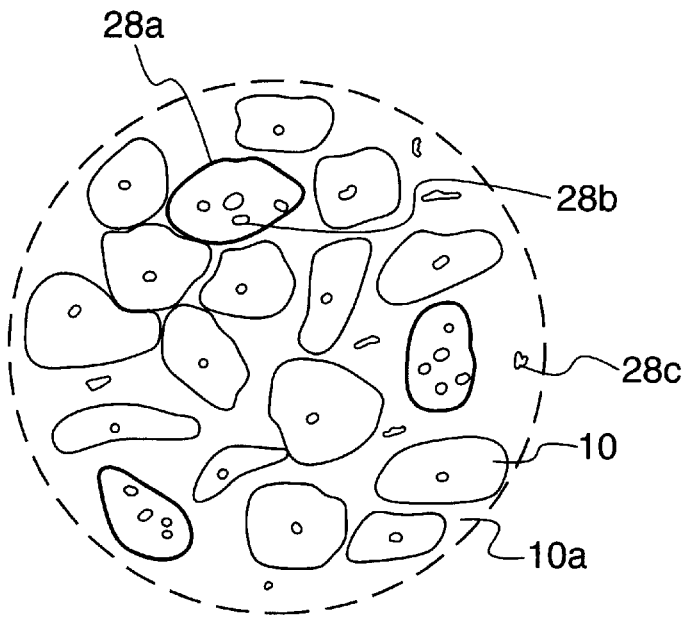
FIG. 3A is an enlarged plan view showing the microenvironment of the encapsulated cells.

The objectives of this procedure are to (a) immunopurify islet cells by removing donor passenger leukocytes; (b) reduce bioburden of leukotropic viruses such as Epstein Bar, CMV, HTLV, and HIV; (c) irrigate islet cell suspension to remove free pathogens across 5 micron filter by vacuum aspiration; and (d) permit adequate exposure to antibiotics in appropriate concentrations to reduce pathogenic organisms. FIG. 3A shows islet cells 10 within an intercellular microenvironment 10a. Donar APC's (MHC Class 11 antigens) 28a, leukotropic viruses 28b and pathogens, like bacterias and fungi, 28c are also present. Entities 28a and 28b are removed by leukoabsorb filter 28. Pathogens 28c pass through the 5 micron filter 32 during irrigation. Any remaining pathogens 28c are killed or inactivated by the antibiotics entrapped within the gel.

EXAMPLE 2

Encapsulation of Islet Cells

Add 10 ml of 2% Na Alginate solution (prepared in tissue culture media such as RPMI 1640 containing 100 mg % glucose), to chamber 30 by syringe through another port 30c. Mix gently to avoid air bubbles. With a final volume of 20 ml, the alginate solution is 1%.

Referring now to FIG. 4B, another 0.45 micron filter 40 is attached to one end 14a of a hollow fiber 14. A valve 42, for example a two-way stop cock, is attached above filter 40. A 50 ml syringe 44 is attached to the other end of stop cock 42. Fiber 14 is dipped through port 30d into chamber 30 containing the Na alginate and islet mixture. While avoiding air bubbles the mixture is aspirated into fiber 14 and through filter 40 into syringe 44. For example, 3 ml of the mixture is aspirated into a 12 inch long fiber having a 2 ml internal volume. Islet cells will be retained in hollow fiber 42 and will be concentrated below filter 40. Valve 42 is closed to prevent flow or leakage of the aspirated material.

Without disturbing the filter/valve assembly at the top of the fiber, dip the 12" long fiber 14 into a vertical 14" measuring jar 46a containing a 250 ml solution of 100 mM CaCl. The CaCl will diffuse through the 30 kDa pores of polysulfone fiber 14 due to its smaller molecular weight and evenly gel the Na Alginate. Allow 10 minutes for gel to form properly. Remove syringe 44, valve 42 and filter assembly 40. Cut fiber 14 into 2" small pieces or other desired length using sterile scalpel and aseptic technique. The gel possesses sufficient stability due to the various G frequencies and block length to remain within the fiber without leaking out.

Next, the open ends of the fiber pieces are contacted with a cross-linking agent like poly-L-lysine, chitosan or polyethylenimine. For example, the ends are dipped into a 1% poly-L-lysine solution for two minutes. A suitable form of poly-L-lysine is available from Sigma. Finally, dip entire fiber pieces in 1% Na Alginate solution (prepared in 0.9% NaCl) contained in another 14" vertical jar 46b. Remove fibers after one minute and re-dip in CaCl solution 46a to gel. This outer gelling makes the fibers extra smooth and provides another layer across the open ends so that the fiber is more biocompatible. Double gelling is expected to dampen and prevent cytokine diffusion.

The device has the following pore characteristics. With a 30 kDa NMWC fiber, approximately 99% of the pores 18 are 30 kDa or less. Almost all of the pores are between 10 and 30 kDa, which represents the smallest pores in the completed device. Suitable fibers may be obtained from A/G Technology Corporation of Needham, Mass.

The poly-L-lysine at the open ends cross-links to the inner islet cell/alginate gel mixture as well as to the outer alginate gel layer to provide pores of 50 kDa or less. The concentration of the poly-L-lysine solution, the molecular weight of the polymer (which can vary between 14,000 and 25,000) and its exposure time determines the degree of cross-linking and may be varied to modify the upper limit. For example, a concentration higher than 1%, or contact time greater than 2 minutes, or larger molecular weight increases cross-linking to create smaller pores. The relationship of these factors to porosity is described in detail in Goosen, "Fundamentals of Microencapsulation", Pancreatic Islet Transplantation Volume III: Immunoisolation of Pancreatic Islets, 21–43, 1994, the contents of which are incorporated herein by reference thereto. Cross-linking on both sides of the poly-L-lysine layer obviates the need for end capping, thereby providing the advantage of reducing the potential for fibroblastic proliferations. The effective pore size distribution over the entire device is between 10 and 50 kDa. This range is beneficial because it prevents donor antigen leakage and cytokine diffusion.

Figure 3B:
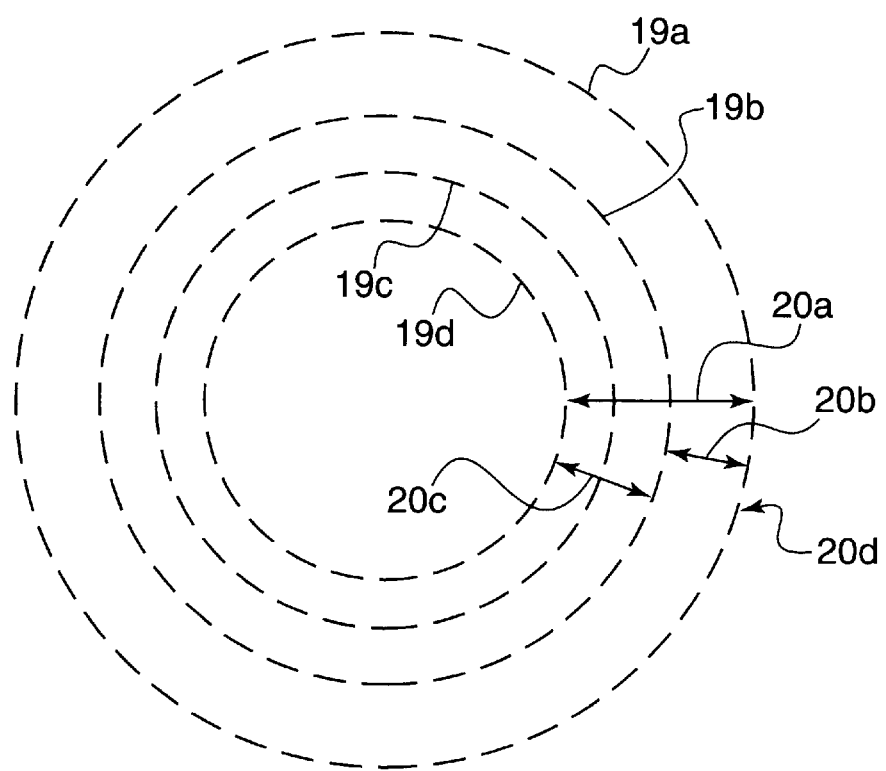
FIG. 3B is a diagram showing the range of pore sizes used in various applications.

FIG. 3B shows relative pore sizes where 19a represents 100,000 Daltons, 19b represents 50,000 Daltons, 19c represents 30,000 Daltons and 19d represents 10,000 Daltons. Typically the prior art has pores in the range of 20a between 10 k and 100 k Da, although range 20b, between 50 k and 100 k Da is most common. The present invention has pores within range 20c, 10 k to 50 k Daltons.

EXAMPLE 3

Assess Packing Efficiency

Next, examine fibers for temperature effect by incubating in 37° C. water bath. The viscosity of alginate declines 2.5% for every 1° C. rise in temperature. Since alginate gelling occurs at 25° C., the examination step is critical to ensure the mechanical integrity of the gel at 37° C. Check for mechanical integrity by squeezing sideways and noting leakage of gel or fluid. Prepare paraffin blocks and examine sections with Dithizone stain to assess packing efficiency of islet cells. Expose to high and low glucose solution to assess the release of insulin/C-peptide and its kinetics. Obtain culture of gelled material for microbial contamination monitoring.

The following steps are used to calculate the packing efficiency of the islet cells aspirated in hollow fiber. Calculate the internal volume of fiber, for example, a one foot long hollow fiber of 3 mm i.d. has a volume of 2120 cmm. Determine the volume of islet cells wherein each cell has a diameter of 150 microns which occupies a volume of 0.0017 cmm. Therefore, the fiber can theoretically contain 2120/0.0017 or 1.2 million cells. Packing density may be varied, as will be explained below.

Before filing, determine the holding volume of one foot hollow fiber of 3 mm i.d. This is done by aspirating solution inside the hollow fiber and then measuring the volume aspirated. Example 2 ml (cell fluid volume).

Determine the number of islet cells present per ml in Na alginate islet cell suspension. This is done by staining a sample of islet suspension fluid with Dithizone stain to identify B cells. Count the cells using a hemocytometer under magnification. In an actual sample there may be 20,000 cells/ml. Aspirate islet cells suspension into fiber using assembly in FIG. 4B. Aspirate islet cell suspension beyond 0.45 micron filter to fill up to 1 ml mark of 50 ml syringe. During aspiration avoid air bubbles. Make sure assembly is securely connected and aspirate the islet cells suspension while gently stirring. Exa. total volume aspirated is 3 ml.

The number of islet cells aspirated into a 1 foot long fiber is calculated by multiplying three factors together as follows:

$$\frac{\text{Islet Cells}}{\text{ml}} \times \text{internal volume of 1 ft. long fiber} \times \frac{\text{Volume Aspirated}}{\text{Internal Volume}}$$

The values are as follows:

$$\frac{20{,}000 \text{ cells}}{\text{ml}} \times 2 \text{ ml} \times \frac{3\text{ml}}{2\text{ml}} = 60{,}000 \text{ cells}$$

Thus, 60,000 cells are contained in a 1 foot long hollow fiber having a 2 ml internal volume. For 120,000 cells, aspirate a total of 6 mls. Packing density is controlled by varying the amount of fluid aspirated above the 0.45 micron filter based on the formula described above.

In neural transplantation, the cell volume requirement is 1/100th of the requirements for type 1 diabetes. The secreted chemicals or hormones have a very short half-life and the target organs are neighboring cells. The encapsulated device may therefore be prepared with a 10–15% tissue density. In transplantations for liver failure, the cell volume requirement is 100 times the requirement for type 1 diabetes.

I have accomplished the objects of my invention by initially immunopurifying the donor cells to increase clinical safety. The cells are suspended within ultrapurified alginate gel inside a hollow polysulfone fiber, two materials which are biocompatible. A cross-linking agent forms a membrane across the fiber ends and the entire fiber is exteriorly gel coated. This provides superior pore control and avoids mechanical end capping which contributes to proper functioning of the encapsulated cells. The outer gel coating and pore control increases clinical safety by reducing adverse host reaction, which occurred in prior art devices. The encapsulated device may be efficiently and cost effectively prepared.

It will be understood that certain features and subcombinations are of utility and may be employed without reference to other features and subcombinations. This is contemplated by and is within the scope of my claims. It is further obvious that various changes may be made in details within the scope of my claims without departing from the spirit of my invention. It is, therefore, to be understood that my invention is not to be limited to the specific details shown and described.

Having thus described my invention, what I claim is:

1. A transplantation or implantation device comprising
    a hollow polysulfone fiber having ends and a fiber wall with a porosity which selectively allows nutritional, gaseous, and metabolic substances to pass therethrough and which only allows passage of substances having a molecular weight less than about 30,000 Daltons, and
    a mixture of viable, somatic, mammalian cells and alginate gel suspended within said fiber.

2. The device of claim 1, wherein said wall is devoid of macrovoids and has a porosity which prevents donor antigens and cytokines from passing through said wall.

3. The device of claim 1, wherein said fiber includes a sulfonic polymer for inhibiting complement activation.

4. The device of claim 1, wherein said somatic cells are selected from the group consisting of neural, endocrine and hepatic cells.

5. The device of claim 1, wherein said cells are substantially free from passenger leukocytes.

6. The device of claim 1, wherein said mixture includes a soluble sulfonic polymer.

7. The device of claim 6, wherein said soluble sulfonic polymer comprises sodium polystrene sulfonate.

8. A transplantation or implantation device comprising
    a hollow polysulfone fiber having ends and a fiber wall with a porosity which selectively allows nutritional, gaseous, and metabolic substances to pass therethrough and
    a mixture of viable, somatic, mammalian cells and alginate gel suspended within said fiber, wherein said alginate comprises ultrapurified alginate which is substantially free of divalent metal toxins and has (i) an endotoxin content of less than 750 EU/g, (ii) a protein content of less than 0.2%, and (iii) a G monomer, dimer and trimer content of greater than 60%.

9. The device of claim 8, wherein said alginate has a viscosity of approximately 322 mPas, a pH of approximately 5.9, a loss on drying factor of approximately 8.7%, a heavy metals content of less than 74 parts per million, an arsenic content of less than 0.5 parts per million, a lead content of less than 7 parts per million, and an iron content of less than 58 parts per million.

10. The device of claim 8, wherein said gel is exposed at the ends of the fiber, and
    wherein the device comprises a porous membrane cross-linked to said exposed gel.

11. The device of claim 10, wherein said porous membrane only allows passage of substances having a molecular weight less than about 50,000 Daltons.

12. The device of claim 11, wherein said porous membrane is selected from the group consisting of poly-L-lysine, chitosan and polyethylenimine.

13. The device of claim 11, wherein said wall has a porosity which only allows passages of substances having a molecular weight less than about 30,000 Daltons.

14. The device of claim 13, wherein said porous membrane is made of poly-L-lysine.

15. The device of claim 10, including an exterior gel coating over said wall and said porous membrane.

16. The device of claim 15, wherein the exterior gel coating cross-links to the porous membrane.

17. The device of claim 15, wherein said porous membrane comprises poly-L-lysine and said gel coating comprises alginate.

18. The device of claim 8, wherein said mixture includes modified Hank's solution devoid of Ca and Mg and enriched with fetal calf serum and adenine.

19. The device of claim 8, wherein said mixture includes antibiotics.

20. The device of claim 19, wherein the antibiotics comprise gentamycin, vancomycin and amphotericin B.

21. The device of claim 19, wherein the antibiotics are selected from the group consisting of gentamycin, vancomycin, amphotericin B, and combinations thereof.

22. The device of claim 21, wherein the cells comprise islet cells.

23. A transplantation or implantation device comprising
    a biocompatible hollow fiber having ends and a fiber wall with a porosity which selectively allows nutritional, gaseous and metabolic substances to pass therethrough and which only allows passage of substances having a molecular weight less than about 30,000 Daltons;
    a mixture of viable, somatic, mammalian cells and a biocompatible viscous carrier disposed within said fiber and exposed at the ends thereof; and
    a biocompatible porous membrane cross-linked to the exposed mixture.

24. The device of claim 23, wherein the porosity of the membrane selectively allows nutritional, gaseous and metabolic substances to pass therethrough.

25. The device of claim 23, wherein said porous membrane is made from a solution containing a cross-linking agent.

26. The device of claim 25, wherein the degree of cross-linking is such as to produce a desired porosity of the membrane.

27. The device of claim 26, wherein the concentration of the cross-linking agent in the solution, the molecular weight of the cross-linking agent, and the contact time between the mixture and the solution are so controlled as to produce a desired degree of cross-linking.

28. The device of claim 27, wherein the solution contains about a 1% volume concentration of between 14,000 and 25,000 molecular weight cross-linking agent and the contact time is about 2 minutes or less.

29. The device of claim 28, wherein said porous membrane has a porosity which only allows passage of substances having a molecular weight less than about 50,000 Daltons.

30. The device of claim 28, wherein the cross-linking agent is selected from the group consisting of poly-L-lysine, chitosan and polyethylenimine.

31. The device of claim 23, wherein said fiber is made of polysulfone.

32. The device of claim 23, wherein said fiber includes a sulfonic polymer for inhibiting complement activation.

33. A transplantation of implantation device comprising
- a biocompatible hollow fiber having ends and a fiber wall with a porosity which selectively allows nutritional, gaseous and metabolic substances to pass therethrough;
- a mixture of viable, somatic, mammalian cells and a biocompatible viscous carrier disposed within said fiber and exposed at the ends thereof, wherein said viscous carrier is ultrapurified alginate which is substantially free of divalent metal toxins and has (i) an endotoxin content of less than 750 EU/g, (ii) a protein content of less than 0.2%, and iii) a G monomer, dimer and trimer content of greater than 60%; and
- a biocompatible porous membrane cross-linked to the exposed mixture.

34. The device of claim 33, wherein said viscous carrier includes a soluble sulfonic polymer.

35. The device of claim 34, wherein said soluble sulfonic polymer comprises sodium polystrene sulfonate.

36. The device of claim 33, wherein said porous membrane comprises poly-L-lysine.

37. The device of claim 33, comprising a outer gel coating covering said fiber and said porous membrane.

38. The device of claim 37, wherein said outer gel coating comprises alginate.

* * * * *